United States Patent [19]

Quick

[11] Patent Number: 4,710,176
[45] Date of Patent: Dec. 1, 1987

[54] NEEDLE DEVICE FOR USE WITH SUBCUTANEOUS CATHETER ASSEMBLIES

[75] Inventor: Richard L. Quick, Trabuco Canyon, Calif.

[73] Assignee: Gish Biomedical, Inc., Santa Ana, Calif.

[21] Appl. No.: 926,506

[22] Filed: Nov. 3, 1986

Related U.S. Application Data

[63] Continuation of Ser. No. 776,379, Sep. 16, 1985, abandoned.

[51] Int. Cl.⁴ .............................................. A61M 5/00
[52] U.S. Cl. .................................... 604/177; 604/180; 604/117; 128/DIG. 26
[58] Field of Search ........................ 604/51, 177–180, 604/175, 272–274, 117; 128/DIG. 26

[56] References Cited

U.S. PATENT DOCUMENTS

| 2,606,555 | 8/1952 | Solomon | 604/180 X |
| 2,727,513 | 12/1955 | Muller | 128/DIG. 26 X |
| 3,046,984 | 7/1962 | Eby | 604/180 |
| 3,856,020 | 12/1974 | Kovac | 604/177 X |
| 4,002,174 | 1/1977 | Reed et al. | 604/239 X |
| 4,129,128 | 12/1978 | McFarlane | 128/DIG. 26 X |
| 4,235,234 | 11/1980 | Whitney et al. | 604/177 X |
| 4,419,094 | 12/1983 | Patel | 128/DIG. 26 X |
| 4,533,349 | 8/1985 | Bark | 128/DIG. 26 |
| 4,631,058 | 12/1986 | Raines | 604/177 X |
| 4,645,495 | 2/1987 | Vaillancourt | 604/180 |

Primary Examiner—Stephen C. Pellegrino
Attorney, Agent, or Firm—Robert J. Schaap

[57] ABSTRACT

A needle device which is designed for use with subcutaneous access catheter assemblies of the type having an interior chamber in which a needle provides fluid access thereto. The needle device of the invention comprises a needle having a vertical shank which is capable of puncturing the skin of a patient and extending into the fluid chamber of the subcutaneous device. An arm is connected to the needle shank through a generally right angled bend and has a fitting adapted for connection to a source of fluid to be introduced into or removed from the chamber of the subcutaneous catheter assembly. A mounting jacket is affixed to the perpendicularly located arm and has a section which extends over the fitting on the end of the arm as well as an integrally formed surface section extending outwardly therefrom and which is capable of being secured to the of the patient by means of a suitable surgical tape or the like. In this way, the needle device can be affixed to the patient for long term use, as for example, intravenous feeding, without the attendant danger of injury to the patient by inadvertent contact with an extended end of the needle device.

22 Claims, 13 Drawing Figures

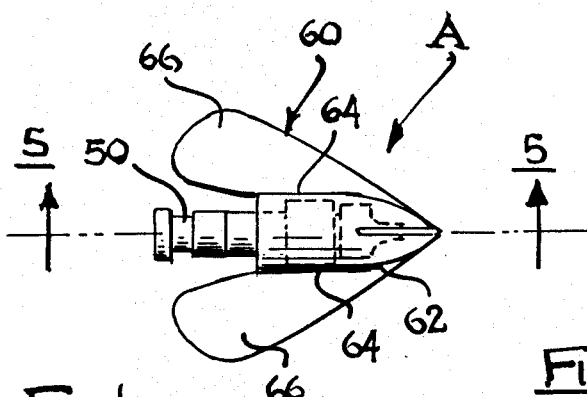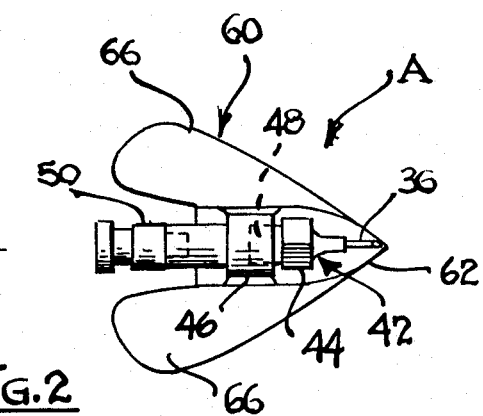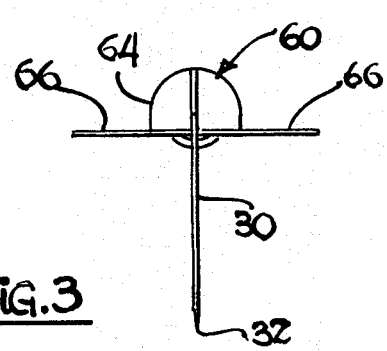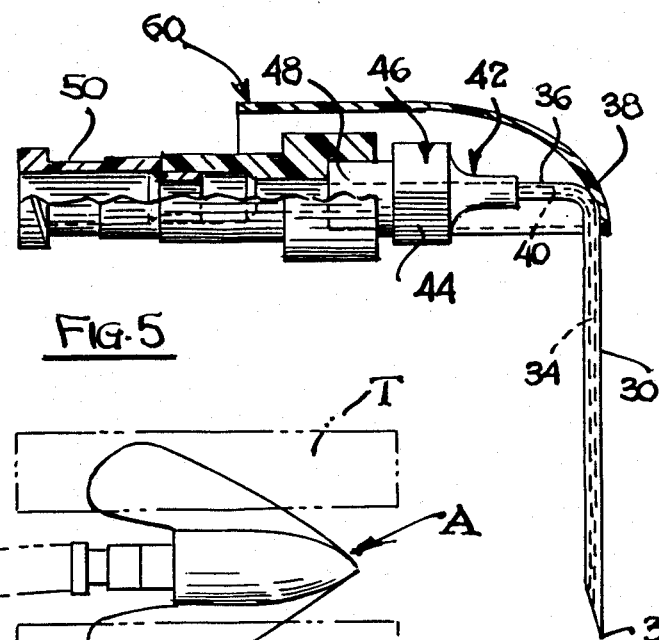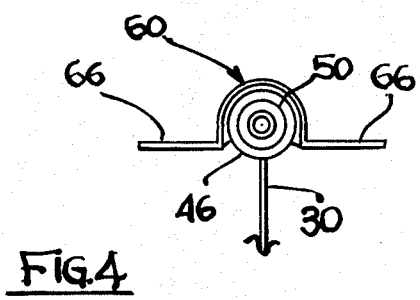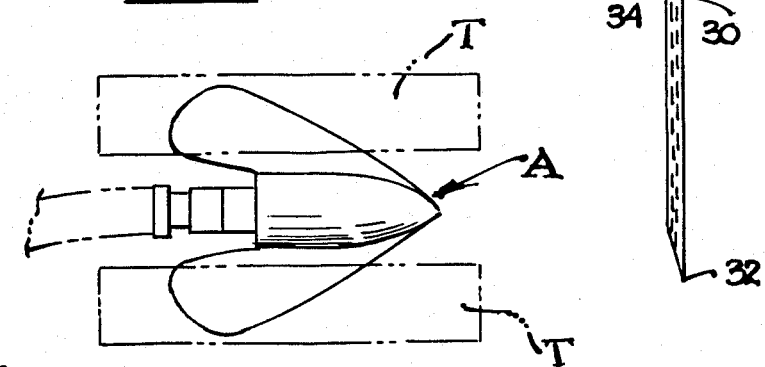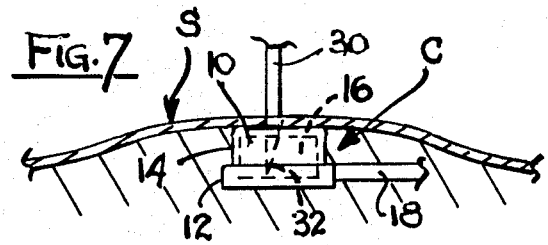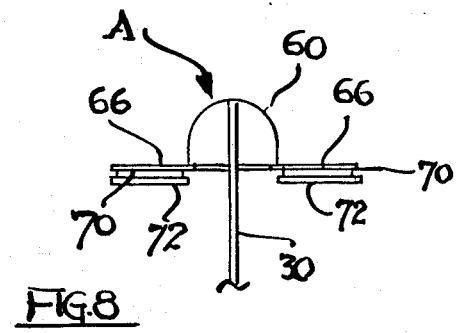

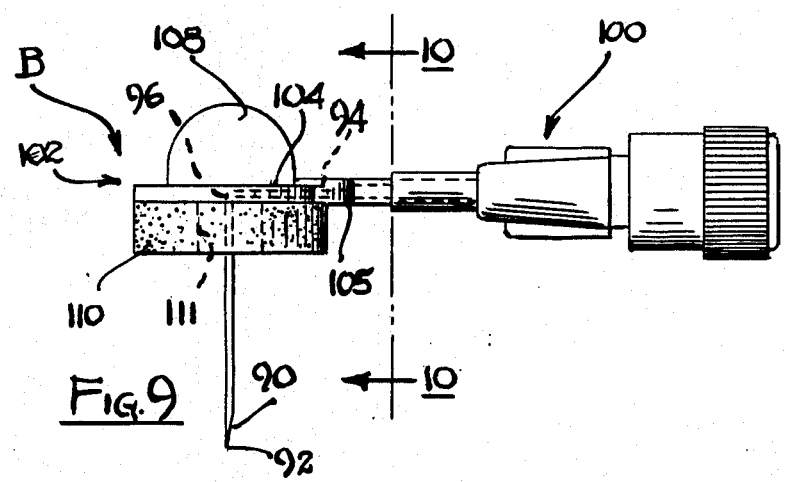
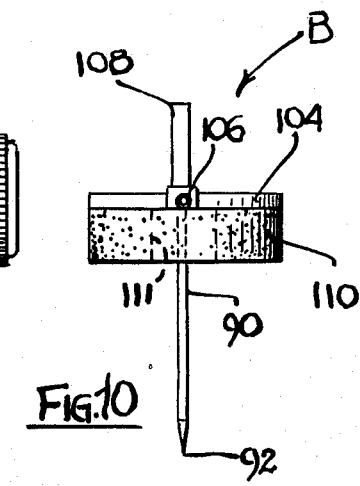
Fig.9  Fig.10
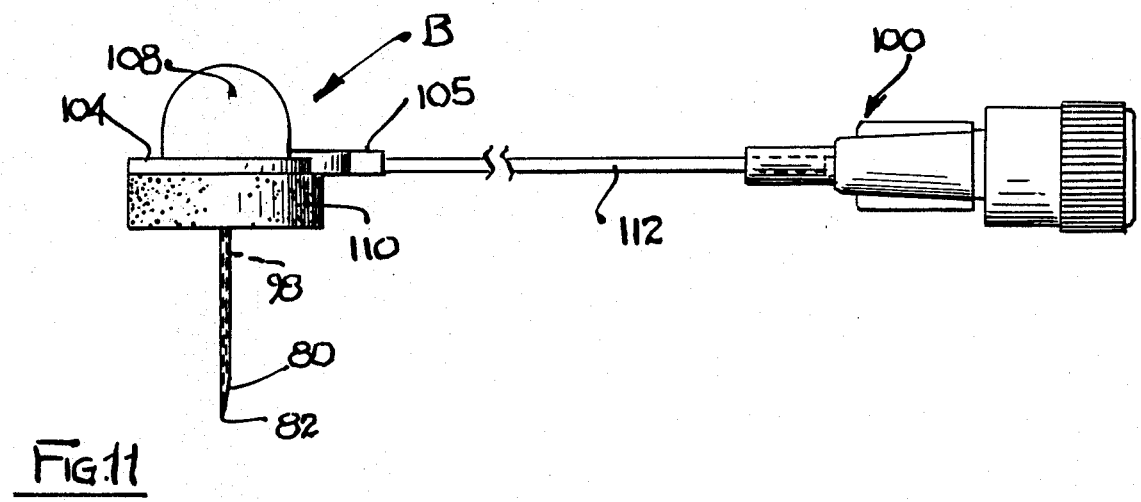
Fig.11
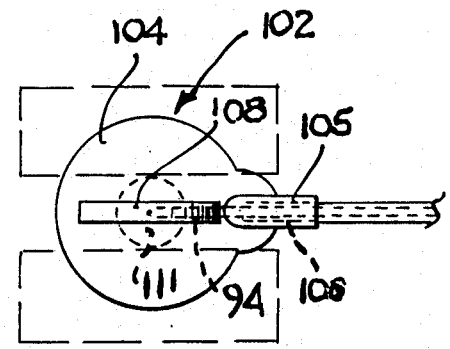
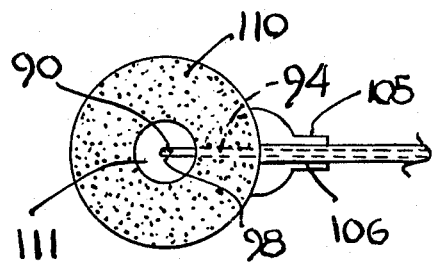
Fig.12  Fig.13

NEEDLE DEVICE FOR USE WITH SUBCUTANEOUS CATHETER ASSEMBLIES

This is a continuation of application Ser. No. 776,379 filed Sept. 16, 1985 now abandoned.

BACKGROUND OF THE INVENTION

1. Field of the Invention

This invention relates in general to certain new and useful improvements in needle devices, and more particularly, to needle devices for use with subcutaneous access catheters and which needle devices include a means to temporarily affix the needle device to the skin of the patient.

2. Brief Description of the Prior Art

In many surgical procedures, it is necessary to provide an internal catheter or so-called "subcutaneous catheter" and which has access to some organ of the body, as for example, the heart. Thus, and in the case of a cardiac catheter, one end may be introduced directly into a ventrical of the heart. The opposite end of the catheter tube, which may be a conventional silicone rubber tube, is connected to a small subcutaneous implanted hat-shape device which contains an internal reservoir. The reservoir may be filled with an intravenous solution or otherwise with medications for the heart or other organ or the like. It is necessary to periodically introduce additional midiciments or fluids into this internal chamber. Moreover, the introduction may occur on a long term basis where the needle would have to penetrate into the chamber and yet protrude from the body for a period of time.

The use of the conventional needle for introducing fluids into the sealed chamber of the subcutaneous catheter assembly creates several problems in that the needle must be affixed to the skin of the patient to prevent any rupture and tear of the patients skin or to prevent any dislodgment as a result of movement of the patient or inadvertent contact with the needle. Generally, the nurses in the hospital or other environment attempt to support the needle by surgical tape. Moreover, gauze may be placed around the needle and then the needle is taped to the patients skin to reduce the amount of movement of the needle. In many cases, it is necessary for the patient to remain perfectly still.

This procedure of implanting a needle results in a potential danger to the patient in that someone could inadvertently contact the needle and push the same thereby rupturing the skin of the patient, if not damaging the subcutaneous catheter. Moreover, it presents a constant hazard in that the nurses or others who attend to the patient must be frequently cautious about inadvertent contact with the needle.

In an attempt to obviate this problem, there have been several proposed "right-angle" needles. That is, needles which have a shank to extend directly into the patients arm, generally perpendicular to the surface of the skin as well as an arm located at right angles thereto. However, here again, it is necessary to secure the needle in some fashion so that the right-angled arm does not move or in effect pivot about the patients skin through rotation of the vertical shank. Here again, the nurses and other attendants have attempted to use surgical tape in order to secure the needle to the patients body. Nevertheless, this means of securement has not been effective inasmuch as the needle is usually formed of a stainless steel and the surgical tape does not efficiently adhesively adhere to the arm of the patient and moreover does not effectively hold the same in a secure position on the skin of the user.

There are several commercially available needles which contain an elongate relatively straight shank and a pair of flanges or similar members secured to and extending outwardly from the needle. Needles of this type are typically referred to as "scalp vein" needles. The flanges on these needles are designed to receive the surgical tape or the like for purposes of securing the tape to the users body. However, the scalp vein needle is adapted to puncture the skin at a very slight angle relative to the skin and, in a manner almost parallel to the surface of the skin. Thus, the use of the flanges on the scalp vein needle has been moderately effective. However, and here again, their effectiveness resides in the fact that the shank of the needle extends into the skin at a very shallow angle relative to the skin.

U.S. Pat. No. 4,380,234 to Kamen discloses an infusion needle attachment which is adapted to effectively guide the unseen portion of a needle into position on the body of the recipient. In this way, the user of the needle is able to judge the desired location at which point the needle should make a physical contact preparatory to subcutaneous administration. The device is not designed for subcutaneous access in the body of the user.

Heretofore, there has not been any effective device for securely holding a needle used with a subcutaneous catheter assembly in a secured position.

OBJECTS OF THE INVENTION

It is, therefore, one of the primary objects of the present invention to provide a needle device which is capable of being used with subcutaneous catheter assemblies and which is capable of being secured to the skin of the user efficiently for long term use to thereby reduce potential danger or injury to the patient.

It is another object of the present invention to provide a needle device of the type stated in which the shank of the needle is capable of penetrating the skin of a patient in a manner generally perpendicular to the skin surface and which permits an angularly located arm thereof to be securely but releasably fastened to the skin of the patient.

It is a further object of the present invention to provide a needle device of the type stated which comprises a somewhat flexible mounting member secured to the needle and which permits attachment to the skin of the body by adhesive tape which extends over outwardly flaring wings on the mounting member.

It is an additional object of the present invention to provide a needle device of the type stated which can be manufactured at a relatively low unit cost in a steril environment but which is highly efficient in operation.

It is still another object of the present invention to provide a method of achieving access to a subcutaneous catheter on a long term basis without the previously accendant hazards to the patient.

With the above and other objects in view, my invention resides in the novel features of form, construction, arrangement, and combination of parts presently described and pointed out in the claims.

BRIEF SUMMARY OF THE DISCLOSURE

A needle device for use with subcutaneous access catheters of the type which are implanted subcutaneously in a patients body and which provides access to some organ of the patients body.

Subcutaneous access catheters of the type with which the needle device of the present invention is effectively used generally comprise a reservoir housing made of a relatively rigid material and which contain an internal sealed reservoir. Intravenous solutions or other medications of the type which are to be introduced into the organ of the patient are provided in this interior sealed chamber. A catheter tube is in communication with and generally extends from this reservoir to the organ of the human body, as for example, the human heart. In this way, medications can be delivered to the human heart directly from this sealed chamber.

Access can be obtained to this sealed chamber by means of intravenous needles which are capable of delivering fluids to or removing fluids from this sealed chamber. The sealed chamber has a wall which is capable of permitting penetration of the point of a needle, but which nevertheless precludes fluid flow through that wall.

The needle device of the present invention comprises a shank having a point adapted to penetrate the skin and also the upper wall of the reservoir and which is generally formed of a stainless steel material. The needle device is integrally formed with an arm which is angularly located with respect to the shank of the needle and which is preferably perpendicularly located with respect to the shank of the needle. In this way, the shank of the needle can penetrate the skin in a direction substantially perpendicular to the skin surface and the arm will lay generally parallel to the skin surface in abutted engagement with the surface of the skin.

A nut or similar fitting is either integral with or secured to the outer end of the arm forming part of the needle device. A luer fitting which is generally formed of a conventional silicone rubber material may be secured to the outer end of this nut or other metallic fitting. This luer fitting is adapted for connection to a conventional external catheter tube or similar tube for delivery of a fluid to the reservoir. In other embodiments the fitting may be connected to the arm through an intermediate catheter tube and need not be part of the needle device.

A mounting jacket extends partially around the arm of the needle device and a portion of the shank which extends generally perpendicularly to the mounting jacket. This mounting jacket has a section which extends over and is secured to the region between the connection of the nut or other metallic fitting to the plastic luer fitting. This jacket also extends over an integral connection of the shank to the perpendicularly located arm.

In one preferred embodiment, the jacket is a generally flat member which has an elongate recess on its undersurface to receive the arm connected to the shank of the needle. This recess is adapted to effectively snap-fit the arm into the jacket and thereby retentively hold the arm and hence the needle in the jacket. In this way, sections of the jacket extend outwardly on opposite sides of the arm and lie in a plane generally parallel to the surface of the skin. Thus, when the needle shank penetrates the skin the surfaces of the jacket disposed on the skin can receive a tape such as a surgical tape for adhesively securing the entire assembly to the skin. Thus, the needle device can be conventionally adhered to the surface of the skin.

In another preferred embodiment of the invention, the mounting jacket includes a semi-cylindrical section which extends over the region between the connection of the nut or other fitting to the plastic luer fitting. A pair of wings are integral with and extend outwardly from the semi-cylindrical section of the jacket generally parallel to and lie in a plane which would be disposed generally parallel to the surface of the skin. In this way, when the shank of the needle penetrates the skin in perpendicular arrangement, the arm of the needle device and the outwardly projecting wings are generally parallel to the surface of the skin and in abutted engagement with the surface of the skin. In addition, these wings are actually somewhat wing-shaped so as to receive a tape, such as a surgical tape. Thus, the needle device can be conventionally adhesively secured to the surface of the skin.

The undersurface of the wings in the one embodiment, or the undersurface of the entire jacket in the other embodiment, could also be provided with an adhesive coating with a releasable backing for attachment to the surface of the skin. Further, a flexible foam pad may be located beneath the jacket and which is compressible so as to provide some confort to the user and also provide a means of adjustability to partially account for different needle length requirements.

The needle device of the invention thereby allows the needle device to be connected to the patient and particularly to the subcutaneous reservoir without the previously encountered inherent dangers to the patient.

This invention possesses many other advantages and has other purposes which may be made more clearly apparent from a consideration of forms in which it may be embodied. These forms are shown in the drawings accompanying and forming part of the present specification. They will now be described in detail, for the purposes of illustrating the general principles of the invention; but it is to be understood that such detailed descriptions are not to be taken in a limiting sense.

BRIEF DESCRIPTION OF THE DRAWINGS

Having thus described the invention in general terms, reference will now be made to the accompanying drawings (two sheets) in which:

FIG. 1 is a top plan view of a needle device constructed in accordance with and embodying the present invention;

FIG. 2 is a bottom plan view of the needle device constructed in accordance with and embodying the present invention;

FIG. 3 is a front elevational view of the needle device constructed in accordance with and embodying the present invention;

FIG. 4 is a rear elevational view of the needle device constructed in accordance with and embodying the present invention;

FIG. 5 is a vertical sectional view taken along line 5—5 of FIG. 1;

FIG. 6 is a top plan view of the needle device of the present invention, similar to FIG. 1, and showing the latter being schematically secured to the surface of a patients skin by adhesive strips;

FIG. 7 is a somewhat schematic vertical sectional view showing the tip of a needle forming part of the needle device of the present invention penetrating the chamber of a subcutaneous access catheter assembly;

FIG. 8 is a front elevational view, somewhat similar to FIG. 4 and showing a modified form of needle device constructed in accordance with and embodying the present invention;

FIG. 9 is a side elevational view of a modified form of needle device constructed in accordance with and embodying the present invention;

FIG. 10 is a front elevational view of the needle device of FIG. 9; and

FIG. 11 is a side elevational view of the needle device, somewhat similar to FIG. 9, and showing a fitting connected to the end of the needle device through an intermediate catheter tube.

DETAILED DESCRIPTION OF PREFERRED EMBODIMENTS

Referring now in more detail and by reference characters to the drawings, A designates a needle device constructed in accordance with and embodying the present invention. This needle device A is generally adapted for use with a subcutaneous catheter assembly, in the assembly C, in the manner as more fully illustrated in FIG. 7 of the drawings.

The catheter assembly C is often referred to as a "subcutaneous catheter" or "subcutaneous catheter assembly" and which is generally conventional in its construction. The subcutaneous catheter assembly is highly effective for either short term use of long term use where it is desired to have a long term feeding or distribution of a fluid to a portion of a patients body and generally at a controlled rate. For example, the subcutaneous catheter assembly C is highly effective during and for intervenous feeding and the like. The needle device A of the present invention is highly effective with the subcutaneous catheter assembly C and is generally designed for use with subcutaneous catheter assemblies. However, the needle device of the present invention is not so limited and can be used in a variety of applications.

The term "long term" with regard to the use of a feeding or distribution of a fluid generally refers to a time frame which is significantly greater than the momentary penetration of the skin by a conventional intravenous needle. Thus, the subcutaneous catheter assembly C may be used, for example, for a period of thirty minutes, one hour, or more.

The subcutaneous catheter assembly C generally comprises an outer enclosed housing 10 mounted on or integrally formed with a base plate 12, in the manner as illustrated in FIG. 7. The housing 10 and base plate 12 may be formed of a relatively rigid plastic material, as for example, a sterilized polyethylene, polystyrene, or the like. Located within the housing 10 is a fluid retaining membrane 14 forming an interior chamber 16 to receive a fluid, such as a glucose solution for intravenous feeding, or a medicament which is designed for time controlled introduction into an organ of the body.

The catheter assembly C is generally located immediately beneath the surface of the skin designated by reference letter S and is implanted in a relatively minor surgical procedure. A small incision is made in the skin allowing the housing 16 to be implanted therebeneath. A catheter tube 18 is connected to an opening in the base plate 12 and is in communication with the interior chamber 16. The catheter tube 18 is of conventional construction and may be formed of a silicone rubber material. Moreover, the opposite end (not shown) of the catheter tube 18 is designed for introduction into a body organ, as for example, the heart of a human being or the like.

The needle device A generally comprises an elongate shank 30 having a needle point at lower end 32, in the manner as illustrated in FIGS. 1 through 5 of the drawings. Moreover, the shank 30 is hollow having an interior bore 34 through which a fluid may pass for introduction into the chamber 16. At its upper end, the needle shank 30 integrally merges into an elongate arm 36 through a right-angled joint 38 so that the arm 36 is generally perpendicularly located with respect to the shank 30 of the needle. The arm 36 and the bend 38 are also provided with an interior bore 40 which is in communication with the bore 34 of the needle shank 30.

The opposite end of the arm 36, that is the left-hand end, as illustrated in FIG. 5 of the drawings, is connected to or is integral with a fitting 42 comprising a nut-like connector 44. The fitting is also provided with an integrally enlarged intermediate section 46 having a rearwardly extending tube receiving boss 48. By further reference to FIGS. 5 and 6, it can be observed that a hollow tube 50, such as another catheter tube, can be connected to and disposed over the boss 48 of the fitting 42. Moreover, the fitting 42 also has a tubular bore 52 in fluid communication with the bore 40 of the arm 36. In this way, fluid can be delivered through the fitting 42 and the needle directly into the interior chamber 16 of the subcutaneous catheter assembly C.

Rigidly secured to the intermediate section 46 of the fitting 42 is a mounting jacket 60, which is more fully illustrated in FIGS. 1–4 and 6 of the drawings. The mounting jacket 60 generally comprises a somewhat triangular forward section 62 which is designed to extend over the fitting 42 and terminates approximately at the point where the arm 36 integrally merges through the bend 38 into the needle shank 30. Moreover, the jacket has somewhat downwardly and outwardly inclined walls 64, particularly in the region of the bend 38 and entirely covers the arm 36 and the bend 38 and a portion of the shank 30 adjacent to the bend 38. The jacket 62 is also integrally formed with a pair of outwardly and rearwardly extending tabs or so-called "wings" 66 which extend along the length of the fitting 42 and beyond the fitting 42, in the manner as illustrated in FIGS. 1, 2 and 6 of the drawings. These tabs 66 are generally parallel to the arm 36 and generally perpendicular to the shank 30.

The jacket 60 is preferably formed of a lightweight plastic material, as for example, polyethylene, polypropylene, or the like.

When it is desired to use the needle device A, the shank 30 penetrates the skin S in a direction generally perpendicular to the surface of the skin, as for example, in the manner as illustrated in FIG. 7. The needle tip thereupon enters into the chamber 16 of the membrane 14 enabling fluid to be introduced into the chamber 14 or withdrawn from the chamber 14. Moreover, for long term use, the wings 66 are facewise disposed on the surface of the skin of the patient. Thus, simple adhesive tape strips T or the like may be used to hold the needle assembly in place on the arm of the patient. In this way, there is no protruding part of the needle assembly which might otherwise be contacted by an attendant or the patient which would jar the needle device and thereby cause damage and potential injury to the patient.

The wings 66 have a sufficient length and width such that conventional surgical tape T can be disposed immediately over the wings to securely hold them in position on the skin of the patient. Nevertheless, the tape T can be easily removed from the surface of the patients skin to enable removal of the wings 66 and hence withdrawal of the entire needle device A.

The undersurface of the jacket 60 is provided with an adhesive or the like for securement to the intermediate section 46 of the fitting 42. Any means for rigidly securing the jacket 60 to the surface of the fitting 46 may be employed.

FIG. 8 illustrates an alternate embodiment of the present invention which does not require the use of the conventional surgical tape T. In the embodiment of the invention as illustrated in FIG. 8, tape strips 70 are permanently mounted on the underside of each of the wings 66 in the manner as illustrated. These tape strips 70 may be provided with releasable backing paper 72 so as to expose the adhesive on the tape strip 70. In this way, the user of the needle device illustrated in FIG. 8, merely removes the releasable backing paper 72, inserts the shank of the needle into the patients skin and merely contacts the skin of the patient with the adhesive coated strip 70.

The surgical needle devices of the present invention are highly effective in use and are disposable. Moreover, they can be packaged in surgical packages which are sealed.

In the device of the present invention, the wings 66 are separated from one another in the manner as illustrated and particularly in FIGS. 1 and 2. In this way, there is some flexibility in the jacket in that each wing 66 can be attached to the skin independently of the other in order to allow for irregular surface contour at the point of attachment.

The wings 66 preferably have a thickness in the range of about 0.035 inches to about 0.070 inches and preferably about 0.060 inches. In this way, the wings, particularly when formed of the preferred materials of construction, as identified above, are somewhat rigid, although still flexible. Nevertheless, they are generally non-bendable and foldable. Thus, when physically attached to the patient, as for example, by means of adhesive strips, the wings provide a fairly tight securement of the needle device so as to accurately hold the same in place.

FIGS. 9–13 illustrate a further embodiment of a needle device B which comprises an elongate shank 90 terminating in a needle point 92. The shank is integrally formed with and extends into an elongate arm 94 through a right angle elbow 96 which integrally connects the arm 94 to the shank 90. Moreover, the shank 90 and the arm 94 are provided with an interior bore 98 and which is located in fluid communication with a fitting 100 on the end of the arm.

Rigidly secured to the arm 94 and the shank 90 is a mounting jacket 102 which comprises a relatively flat sheet 104 of a somewhat flexible and bendable plastic material. The sheet 104 has an intergrally formed rearwardly and upwardly extending projection 105 which has some thickness so as to be formed with a longitudinally extending forwardly opening channel 106. By reference to FIG. 13, it can be observed that this channel 106 extends from one of the sides of the sheet 102 toward the center thereof. The channel 106 is sized to snuggly and retentively receive the arm 94 of the needle such that the shank 90 extends downwardly from approximately the center portion of the sheet 104. Inasmuch as the downwardly opening portion of the channel has a smaller width than the interior portion, the arm 94 can be retentively held therein.

Integrally formed on the upper surface of the sheet 104 is a flange 108 for engagement by the fingers of a user. In this way, the needle device can be easily manipulated by a user thereof. Mounted on the undersurface of the jacket 102 is a pad 110 formed of a somewhat flexible and yieldable foam-like material, such as a polyurethane foam. The pad is formed with a centrally located hole 111 to accommodate the needle shank 90.

The needle device can be positioned on a patient and the shank 90 extended through the skin of a patient. The foam pad 110 will provide some cushioning. Moreover, adhesive tape strips can be placed over the extended portions of the jacket 102 along the longitudinal sides of the arm 94, in the manner as illustrated in FIG. 12.

FIG. 11 illustrates a modified embodiment of the needle device of the present invention and is similar to the needle device illustrated in FIGS. 9 and 10. In this embodiment, the fitting 100 is separated from the needle device, but connected thereto through an intermediate catheter tube 112. Thus, it can be observed that the fitting 100 does not have to be rigidly secured to the end of the arm but can be displaced therefrom although in fluid communication therewith. Separation of the fitting 100 from the actual needle device is advantageous in that much less structural material is placed around the area of penetration of the needle into the patients body. Thus, the entire device is smaller and this facilitates ease of use. Further, it significantly reduces discomfort to the patient when connecting and disconnecting tubes from other sources of fluid to the fitting.

The pad 110, due to its compressible nature, provides a type of height adjustment. In many cases, the implanted device may be located at differing depths with respect to skin surface. For example, in the case of some individuals having a substantial amount of fatty tissue under their skin, the implanted device may be located at a significantly greater depth than in other individuals. Thus, while the depth of the implanted device in the depth of the implanted device which may vary from individual to individual, the desired length of the needle shank may vary and the pad 110 will serve to take some of the differences. Thus, in the case of an individual where the depth of the implanted device is close to the surface of the skin, the foam pad will not compress to a substantial degree.

Thus, there has been illustrated and described a unique and novel needle device which is capable of being releasably secured to a patient and which thereby fulfills all of the objects and advantages which have been sought for this device. It should be understood that many changes, modifications, variations and other uses and applications will become apparent to those skilled in the art after considering this specification and the accompanying drawings. Therefore, any and all such changes, modifications, variations and other uses and applications, which become apparent to those skilled in the art, after considering this specification and the accompanying drawings, are deemed to be covered by the invention which is limited only by the following claims.

I claim:

1. A needle device adapted for use with a subcutaneous implanted assembly having a fluid reservoir, said device comprising:
   (a) a tubular needle shank of the type used with a subcutaneous implanted fluid reservoir and having a tip portion adapted to extend through the skin and into the fluid reservoir, said shank having a bore through which fluid may enter or be withdrawn from said reservoir;

(b) a tubular arm angularly located with respect to said shank and being integrally connected to said shank, said arm having a bore in fluid communication with the bore of said shank, (c) a mounting jacket extending partially around a portion of said arm and being secured to said arm, said jacket extending outwardly transversely from said arm and which is capable of being flatwise disposed on the surface of the skin adjacent to the region where the shank penetrates the skin so that tape may be adhesively secured to the jacket and to the skin to retentively hold the needle device in a fixed position onto the user without the necessity of independently tapeing the arm to the user's skin, and (d) an upstanding section on said jacket and being substantially rigid so that it can be grasped by an attendant with one hand and positioned with respect to a user and properly maneuvered to insert the tip portion through the user's skin and into the fluid reservoir.

2. The device of claim 1 further characterized in that said jacket is a somewhat flexible sheet of material having an arcuate section with downwardly and outwardly extending walls which merge into said flat surfaces, said arcuate section forming the recess on the undersurface of the jacket to snugly receive and hold the arm.

3. The device of claim 2 further characterized in that said shank and arm are formed of a metal and said jacket is formed of a plastic material.

4. The device of claim 1 further characterized in that said jacket comprises a pair of wings which extend transversely outwardly to receive strips of adhesive tape, and said wings presenting the flat surfaces.

5. The device of claim 4 further characterized in that said wings are integral with said jacket.

6. The device of claim 1 further characterized in that said arm perpendicularly located with respect to said shank.

7. The device of claim 1 further characterized in that said jacket is adhesively secured to said arm.

8. The device of claim 1 further characterized in that said jacket extends around a substantial portion of the length of said arm.

9. The device of claim 1 further characterized in that said mounting jacket has a recess in its undersurface to receive the tubular arm, said jacket being formed of a material which is flexible but which has sufficient rigidity so that the portion of the jacket around said recess retentively holds the tubular arm, said jacket having flat surfaces extending beyond both sides of said recess, and which surfaces are capable of being flatwise disposed on the surface of the skin adjacent to the region where the shank penetrates the skin.

10. The device of claim 1 further characterized in that a foam pad is disposed on the underside of said jacket to be disposed between the users skin and a portion of the arm, said pad having an enlarged aperture which receives the needle shank and is substantially larger than the needle shank.

11. The device of claim 10 further characterized in that said jacket is formed of a transparent material.

12. The device of claim 1 further characterized in that
(a) an intermediate flexible catheter tube is connected at one end to one end of said tubular arm, and
(b) a luer type fitting is connected to the other end of said intermediate tube and adapted to have a catheter tube connected thereto.

13. A needle device adapted for use with a subcutaneously implanted assembly having a fluid reservoir, said device comprising:

(a) a tubular needle shank of the type used with a subcutaneous implanted fluid reservoir and having a tip portion adapted to extend through the skin and into the fluid reservoir, said shank having a bore through which fluid may enter or be withdrawn from said reservoir, (b) a tubular arm angularly located with respect to said shank and being integrally connected to said shank, said arm having a bore in fluid communication with the bore of said shank, and (c) a mounting jacket extending partially around a portion of said arm and being secured to said arm, said jacket extending outwardly transversly from said arm and which is capable of being flatwise disposed on the surface of the skin adjacent to the region where the shank penetrates the skin so that tape may be adhesively secured to the jacket and to the skin to retentively hold the needle device in a fixed position onto the user without the necessity of independently tapeing the arm to the users skin, said jacket being configured so that it can be grasped by an attendant and positioned with respect to a user and properly maneuvered to insert the tip portion through the users skin and into the fluid reservoir.

14. The needle device of claim 13 further characterized in that said tubular shank is adapted to pierce the skin of a user and to extend into the body in a direction substantially perpendicular to the skin surface.

15. The device of claim 14 further characterized in that said shank and arm are formed of a metal and said jacket is formed of a plastic material.

16. The needle device of claim 13 further characterized in that said mounting jacket has a recess on its undersurface to receive the tubular arm, and said jacket being formed of a material which is flexible but which has sufficient rigidity so that the portion of the jacket around said recess retentively holds the tubular arm.

17. The device of claim 13 further characterized in that a relatively compressible foam pad is located on an undersurface of said jacket and partially compensates for different shank length requirements as a result of its compressibility.

18. The device of claim 13 further characterized in that said jacket is a somewhat flexible sheet of material having an arcuate section with downwardly and outwardly extending walls which merge into said flat surfaces, said arcuate section forming the recess on the undersurface of the jacket to snugly receive and hold the arm.

19. The device of claim 13 further characterized in that said jacket comprises a pair of wings which extend transversely outwardly to receive strips of adhesive tape, and said wings presenting the flat surfaces.

20. The device of claim 19 further characterized in that said wings are integral with said jacket.

21. The device of claim 13 further characterized in that said jacket is adhesively secured to said arm.

22. The device of claim 13 further characterized in that:
(a) an intermediate flexible catheter tube is connected at one end to one end of said tubular arm, and
(b) a luer type fitting is connected to the other end of said intermediate fluid tube and adapted to have a catheter tube connected thereto.

* * * * *